(12) United States Patent
Zamir et al.

(10) Patent No.: US 6,222,053 B1
(45) Date of Patent: *Apr. 24, 2001

(54) SEMI-SYNTHESIS OF A PROTECTED BACCATIN III COMPOUND

(75) Inventors: Lolita Zamir, Westmount; Gaétan Caron, Laval, both of (CA)

(73) Assignee: Institut National de la Recherche Scientifique, Quebec (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/951,786

(22) Filed: Oct. 17, 1997

(30) Foreign Application Priority Data

Oct. 18, 1996 (CA) .................................................. 2188190

(51) Int. Cl.[7] .................................................. C07D 305/14
(52) U.S. Cl. .......................................... 549/510; 549/511
(58) Field of Search ..................................... 549/510, 511

(56) References Cited

U.S. PATENT DOCUMENTS

| Re. 34,277 | 6/1993 | Denis et al. | 549/510 |
|---|---|---|---|
| 5,019,504 | 5/1991 | Christen et al. | 435/123 |
| 5,352,806 * | 10/1994 | Gunawardana et al. | 549/510 |
| 5,380,916 | 1/1995 | Rao | 560/107 |
| 5,405,972 | 4/1995 | Holton et al. | 549/214 |
| 5,407,674 | 4/1995 | Gabetta et al. | 424/195.1 |

OTHER PUBLICATIONS

Li, J.–y. et al., "Endophytic taxol–producing fungi from bald cypress, *Taxodium distichum*, "*Microbiol.* 142:2223–2226 (1996).

Ojima, I. et al., "New and Efficient Approaches to the Semisynthesis of Taxol and Its C–13 Side Chain Analogs by Means of β–Lactam Synthon Method," *Tetrahedron* 48:6985–7012 (1992).

Ojima, I. et al., "A Highly Efficient Route to Taxotere by the β–Lactam Synthon Method," *Tetrahedron Letts.* 34:4149–4152 (1993).

Zamir, L.O. et al., "Taxanes isolated from *Taxus canadensis*," *Tetrahedron Letts.* 33:5173–5176 (1992).

* cited by examiner

*Primary Examiner*—Ba K. Trinh
(74) *Attorney, Agent, or Firm*—Sterne, Kessler, Goldstein & Fox P.L.L.C.

(57) ABSTRACT

The present invention relates to a semi-synthetic process to convert a naturally occurring taxane into a suitable starting material for the synthesis of paclitaxel and related compounds. Specifically, the present invention relates to a process for the conversion of 9-dihydro-13-acetylbaccatin III into a 7-protected baccatin III which can then be used as starting material for the synthesis of taxane derivatives such as paclitaxel, docetaxel, cephalomannine and other taxanes structurally related to baccatin III. The method as described uses a preparative scale technique which is amenable to commercial scale-up.

10 Claims, 3 Drawing Sheets

SEMI-SYNTHESIS OF A PROTECTED BACCATIN III COMPOUND

FIELD OF THE INVENTION

The present invention relates to a semi-synthetic process to convert a naturally occurring taxane into a suitable starting material for the synthesis of paclitaxel and related compounds. Specifically, the present invention relates to a process for the conversion of 9dihydro-13-acetylbaccatin III into a 7-protected baccatin III which can then be used as starting material for the synthesis of taxane derivatives such as paclitaxel, docetaxel, cephalomannine and other taxanes structurally related to baccatin III. The method as described uses a preparative scale technique which is amenable to commercial scale-up.

BACKGROUND OF THE INVENTION

The taxane family of terpenes is considered to be an exceptionally promising group of cancer chemotherapeutic agents. Many taxane derivatives, including paclitaxel, docetaxel, taxcultine canadensol are highly cytotoxic and possess strong in vivo activities in a number of leukemic and other tumor systems. Paclitaxel, and a number of its derivatives, have been shown to be effective against advanced breast and ovarian cancers in clinical trials (W. P. MacGuire et al., *Annals of Internal Medicine*, vol 111, pg. 273, 1989). They have also exhibited promising activity against a number of other tumor types in preliminary investigations. Paclitaxel has recently been approved in the U.S. and Canada for the treatment of ovarian cancers (Rose et al., in *"The Alkaloids"*, A Brossi, Ed., Academic Press, New York, Paclitaxel: A Review of its preclinical in vivo Anti-tumor Activity. Anti-Cancer Drugs 3, 311–321 1992; and Suffness, M., Paclitaxel: from discovery to therapeutic use. Ann. Rep. In Med. Chem, 28, 305–314, 1993). Taxanes are believed to exert their antiproliferative effect by inducing tubulin polymerization, which forms extremely stable and nonfunctional microtubules (Schiff, et al., Promotion of Microtubule Assembly in vitro by Paclitaxel. Nature, 277, 665–667, 1979). However, a major problem with the clinical studies is the limited availability of paclitaxel and its derivatives.

Taxanes are natural products which can be isolated from yew trees. The first taxane to be characterized was paclitaxel (also known as taxol™) which was isolated and purified from the bark of the Pacific yew in 1971. The only available natural source of paclitaxel to date are several species of a slow growing yew (genus Taxus), wherein paclitaxel is found in very low concentrations (less than 400 parts per million) in these trees. Furthermore the extraction is difficult, the process is expensive and the yield of paclitaxel is low (Huang el al, J. Nat. Prod. 49 665, 1986, reported a yield of 0.00025% of a crude paclitaxel fraction from Taxus brevifolia bark).

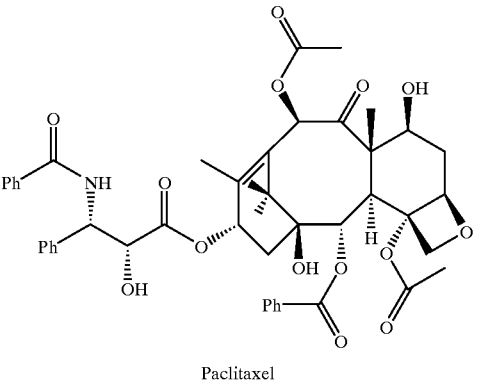

Paclitaxel

Paclitaxel can be isolated from the bark of *Taxus brevifolia*, the pacific yew tree, or from *Taxus baccata*, its European relative. Since removal of the bark destroys the trees and endangers the species, isolation of taxanes from the stems and needles of various Taxus species offers hope that the supply of taxanes, in particular paclitaxel, would become more abundant.

The preparation of paclitaxel derivatives, some of which have been reported to demonstrate enhanced chemotherapeutic activity, ultimately depends upon the supply of the parent compound—baccatin III. The structure of baccatin III has the basic diterpenoid structure of paclitaxel without the side chain at the C-13 position.

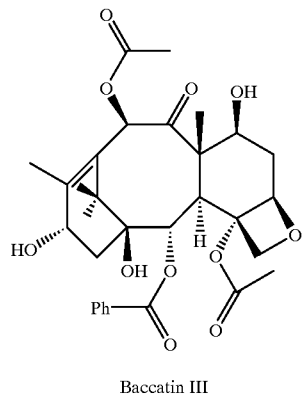

Baccatin III

Baccatin III is an important starting material in paclitaxel semi-synthesis. Therefore the significance of baccatin III will likely increase as more clinical studies are performed using paclitaxel. One such reason is that it appears that water soluble paclitaxel-like compounds with slightly modified C-13 side chains may be more desirable as cancer chemotherapeutic agents than the naturally occurring less water soluble paclitaxel. This increases the urgent need for baccatin III as a starting material to synthesize both paclitaxel and second or third generation paclitaxel-like compounds. There is, therefore, a need for an improved method of isolating and/or synthesizing Baccatin III.

The majority of research to date has been concerned with the development of techniques to increase the availability of either paclitaxel or baccatin III. These techniques have included improvements to the isolation and purification processes (U.S. Pat. No. 5,407,674 and U.S. Pat. No. 5,380,916), to the total synthesis (U.S. Pat. No. 5,405,972) and partial synthesis (from more abundant paclitaxel precursors) and also isolation from a variety of cell culture systems U.S. Pat. No. 5,019,504). In Addition, an endophytic fungi isolated form bald cypress (*Taxodium distichum*) was reported to produce very small amounts of paclitaxel (Strobel, R. et al., Microbiology, 142, 2223–2226, 1996)

Because of the structural complexity of paclitaxel, partial synthesis is a far more viable approach to providing adequate supplies of paclitaxel and paclitaxel precursors than total synthesis. The first successful semi-synthesis of paclitaxel was developed by Denis et al, (U.S. Pat. No. 4,924,011 re-issued as U.S. Pat. No. 34,277), using the starting material 10-deacetylbaccatin III which can be extracted in relatively high yield from the needles of specific species.

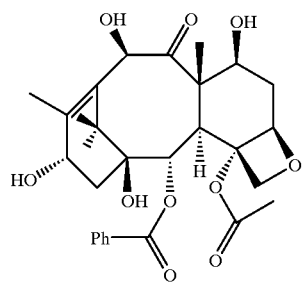

10-deacetylbaccatin III

In fact, most of the research to date regarding the semi-synthesis of paclitaxel has involved 10-deacetylbaccatin III. The conversion of 10-deacetylbaccatin III into paclitaxel is typically achieved by protecting the hydroxy at C-7, attachment of an acetyl group at the C-10 position, attachment of a C-13 β-amido ester side chain at the C-13 position through esterification of the C-13 alcohol with the β-lactam moiety, and deprotecting C-7. Since the supply of 10-deacetylbaccatin III is limited, other sources should be pursued.

Research has recently centred on semi-synthesis of paclitaxel from 10-deacetylbaccatin III because it is the major metabolite obtained from specific species of the European Yew (*Taxes baccata*). However to date, the yields of 10-deacetylbaccatin III have been unsatisfactory, ranging from 50–165 mg taxane per kilogram of starting material (i.e. providing yields of between 0.005 to 0.017%). Hence there is an urgent need for novel semi-synthetic techniques to produce higher yields of paclitaxel precursors, such as baccatin III, for subsequent use in the production of paclitaxel derivatives. The present invention provides such a method, describing the conversion of a known taxane (9-dihydro-13-acetylbaccatin III), which is produced as a major metabolite in a certain species of taxus, into a paclitaxel precursor which produces relatively large amounts of a 7-protected baccatin III. Depending on the collection sites, the yield of 9-dihydro-13-acetylbaccatin III can vary from 2.0 to 2.5 g per kilogram of dry plant and this taxane can be chemically transformed, by the present invention, into 7-protected baccatin III in 20% yield.

SUMMARY OF THE INVENTION

The present invention is directed towards a new method of producing a 7-protected baccatin III, from a naturally occuring taxane (9-dihydro-13-acetylbaccatin III) which is produced in high yields in *Taxus canadensol*. The 7-protected baccatin III can be used as a starting material for the synthesis of paclitaxel and paclitaxel derivatives.

Accordingly, it is an object of this invention to provide a reproducible method for the semi-synthesis of 7-protected baccatin III from the naturally occurring compound, 9-dihydro-3-acetylbaccatin III, isolated from plant matter derived from the Taxus genus of plants.

It is a further object of this invention to provide a method for the semi-synthesis of baccatin III, and other protected intermediates, that proceeds with higher yields than currently known methods.

Still a further object is to provide a simple, inexpensive method of preparing 7-protected baccatin III that proceeds at room temperature.

It is also an object of this invention to provide a method for the semi-synthesis of 7-protected baccatin III, from plant matter that is on a preparative scale which is amenable to commercial scale-up processes.

The present invention provides a process for the preparation of a taxane of formula (III)

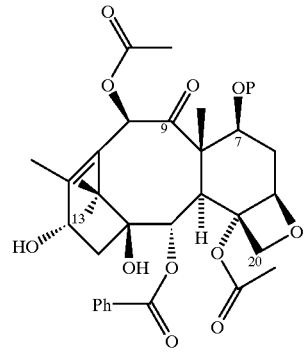

which comprises the steps of: (i) protecting a hydroxy group at the 7-position of 9dihydro-13-acetylbaccatin III; (ii) oxidizing a hydroxy group at the 9-position of 7-protected 9-dihydro-13-acetylbaccatin; (iii)deacylating an ester at the 13-position to form a 13-hydroxy compound of formula III, wherein P is a hydroxy protecting group. The present invention provides an additional step of removing the hydroxy protecting group P at the 7-position to yield baccatin III.

The present invention provides a process for the preparation of a 7-protected-9-dihydro-13-acetylbaccatin of formula I.

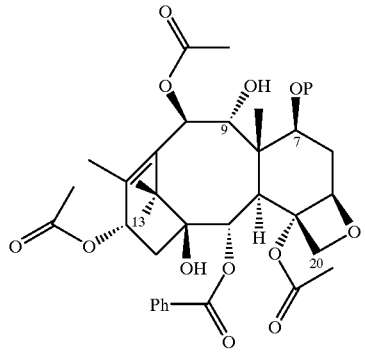

wherein P is a hydroxy protecting group, which comprises the step of reacting 9-dihydro-13-acetylbaccatin III with a hydroxy protecting group to form a compound of formula I.

The present invention also provides a process for the preparation of a compound of formula II

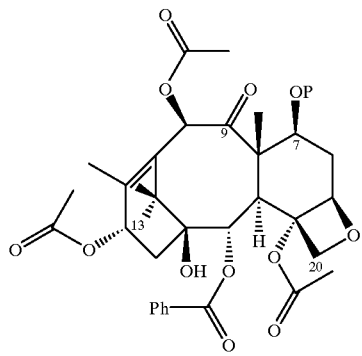

II

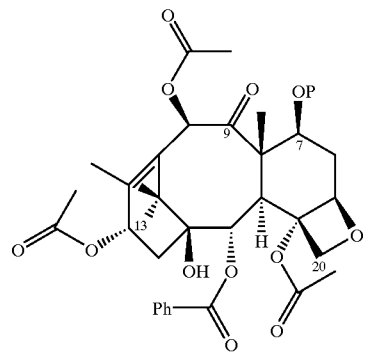

II

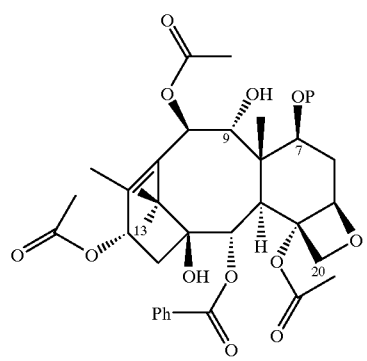

I which comprises the step of oxidizing a compound of formula I.

The present invention further provides a process for the preparation of a compound of formula III from a compound of formula II

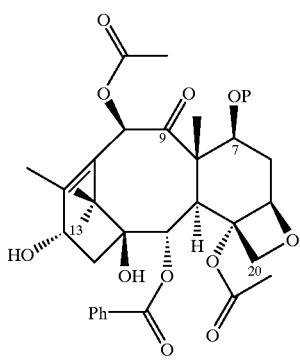

III wherein P is a hydroxy protecting group, which comprises converting a 13-acetyl group to 13-hydroxyl group of a compound of compound of formula II.

In a preferred embodiment 7-protected-9-dihydro-13-acetylbaccatin is formed by reacting 9-dihydro-13-acetylbaccatin III with a silylhalide, benzylhalide or alkylhalide, the halide is selected from Cl, Br, or I. Preferred protecting reagents are t-butyldiphenylsilylchloride, t-butyldimethylsilylchloride, triethylsilylchloride or triisopropylsilylchloride.

In a preferred embodiment the oxidation is facilitated by Jones' reagent, pyridinium dichromate, a Swern oxidation, a permanganate ion or Sarret's reagent.

In a preferred embodiment deacylation is facilitated by reaction with an alkylalkalimetal or arylalkalimetal reagent. Most preferred regent for deacylation is n-butyllithium.

These and other objects, as well as the nature, scope and utilization of this invention, will become readily apparent to those skilled in the art from the following description, the drawings and the appended claims.

BRIEF DESCRIPTION OF THE DRAWINGS

The present invention is disclosed in connection with the appended drawings, in which.

DETAILED DESCRIPTION OF INVENTION

Figure 1:
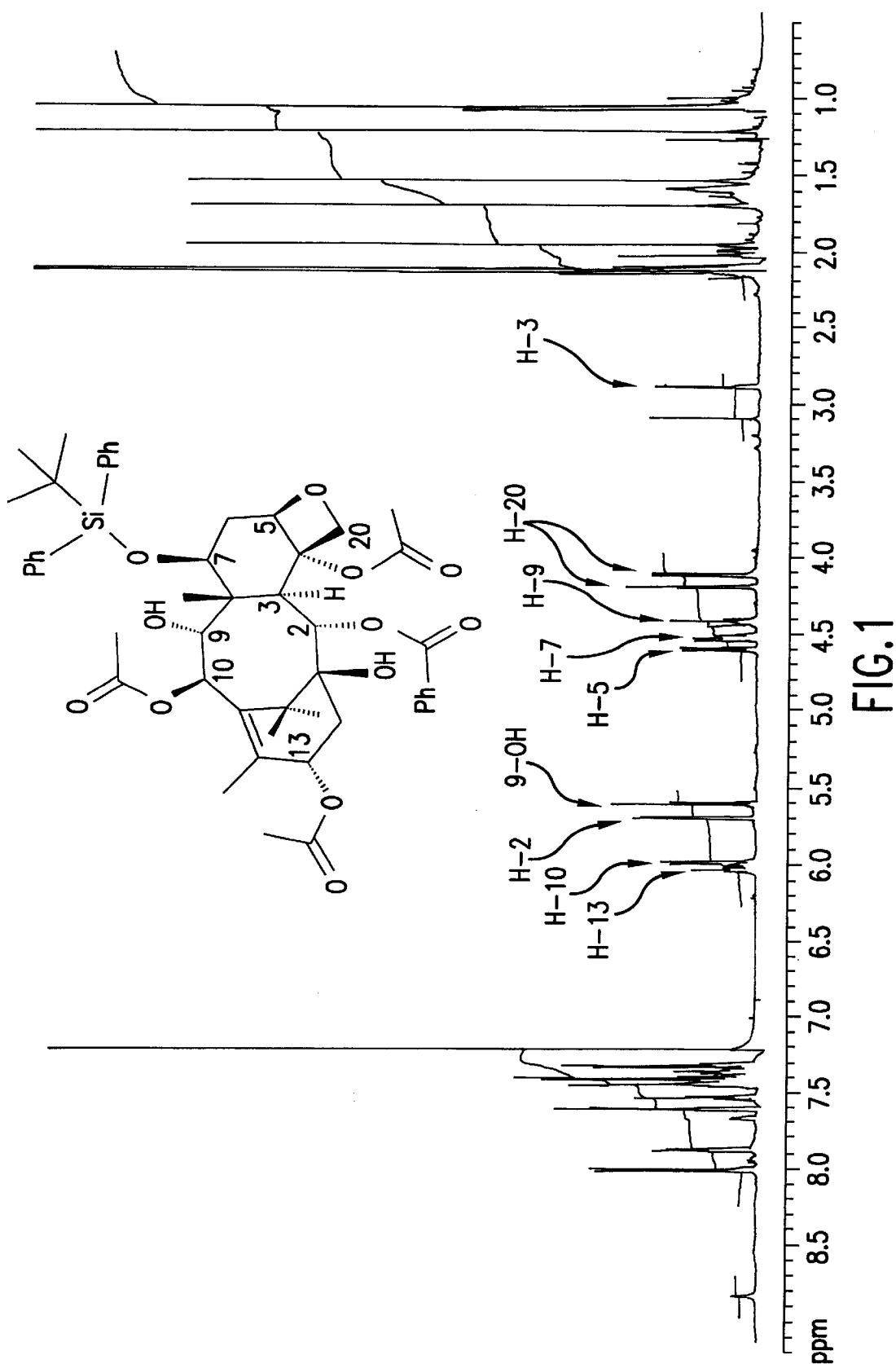
FIG. 1 shows NMR spectra of an example of Compound 2, 9-dihydro-13-acetyl-7-t-butyldiphenylsilyl-baccatin III.
Figure 2:
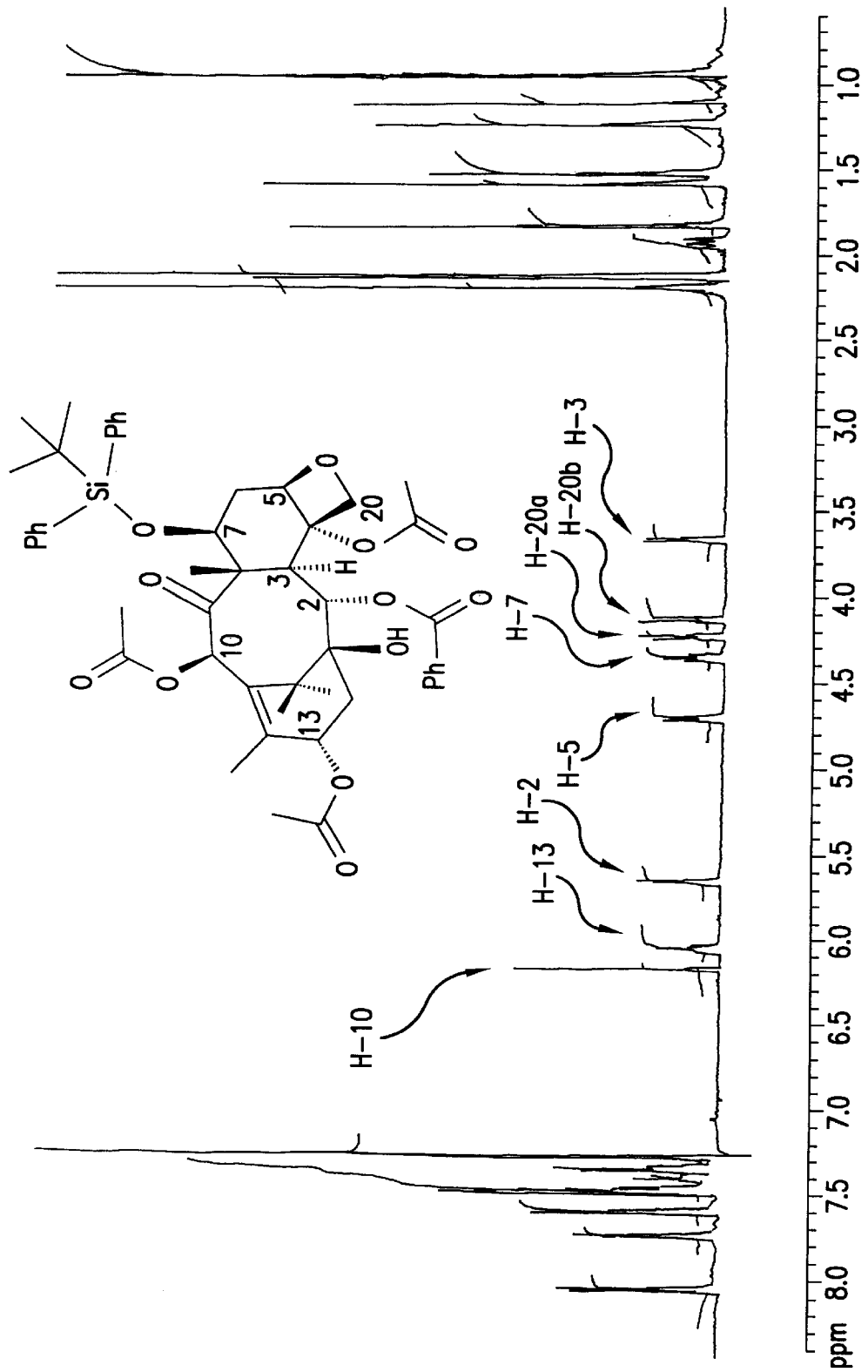
FIG. 2 shows NMR spectra of an example of Compound 3, 13-acetyl-7-t-butyldiphenyl-silyl-baccatin III.
Figure 3:
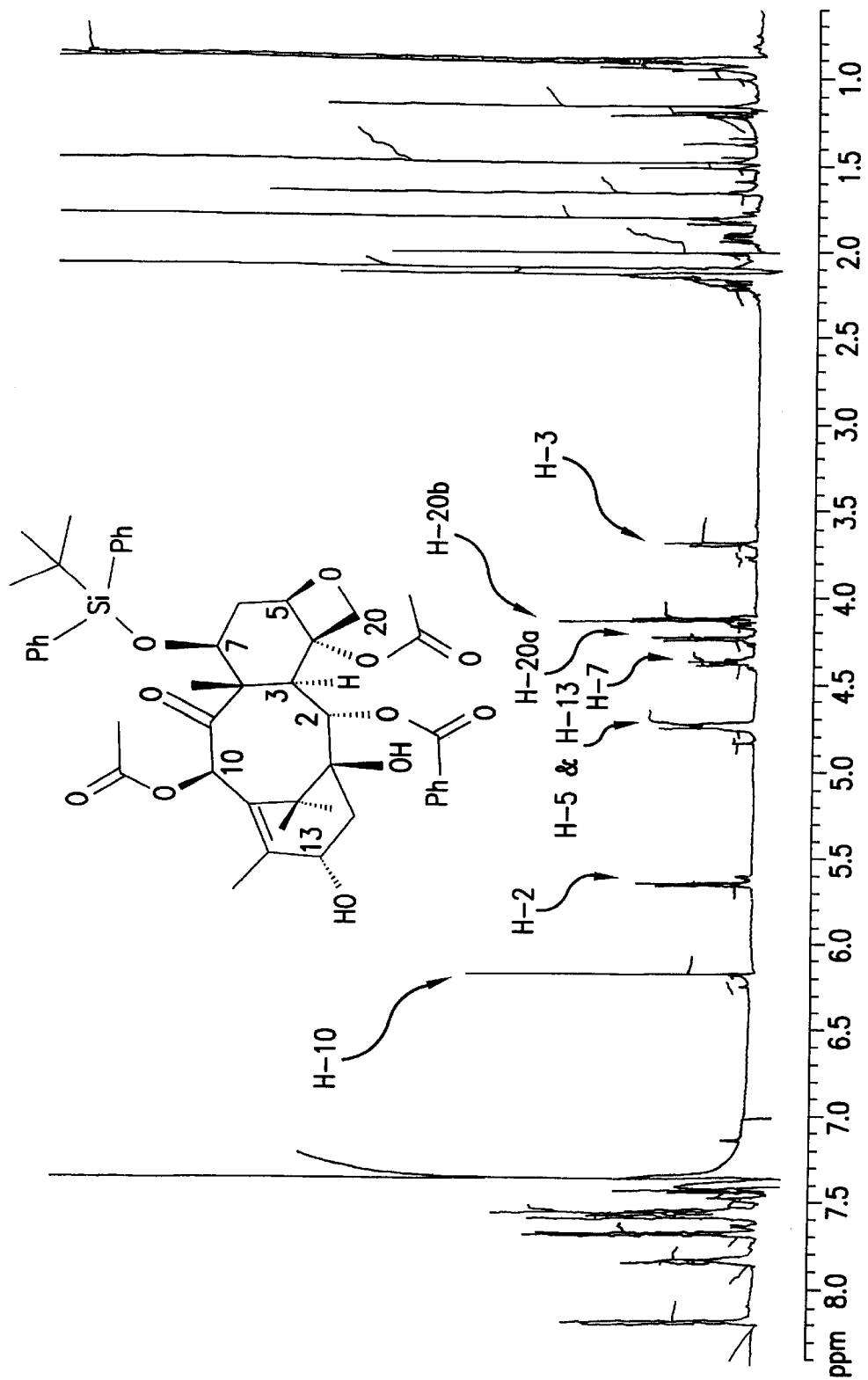
FIG. 3, shows NMR spectra of an example of Compound 4, 7-tert-butyldiphenylsilylbaccatin III.

The present invention relates to a high yield process for converting 9-dihydro-13-acetylbaccatin III (an abundant taxane found in *T. canadensis* needles), into a 7-protected baccatin III, which can subsequently be used as starting material for the synthesis of paclitaxel and related compounds.

The starting material for use in this invention is vegetal material selected from a group of plants commonly referred to as taxads. The most suitable plants of this group are the species Taxus. Amongst the Taxus species, *Taxus canadensis* is a preferred source for use in the semi-synthetic method claimed in the present invention and differs from other yews both in its physical appearance (it is a small ramping evergreen bush), and in the composition of some of its taxanes. Paclitaxel, cephalomannine and 10-deacetylbaccatin III can be isolated from *Taxus canadensis* which are also found in most if not all other yews. *Taxus canadensis* is, however, the only yew presently known which accumulates a significant quantity of 9-dihydro-13-acetyl baccatin III in its needles, wherein it is found in concentrations 3–7 times greater than paclitaxel (Zamir L. O. et al. Tetrahedron Letters 33 5173, 1992).

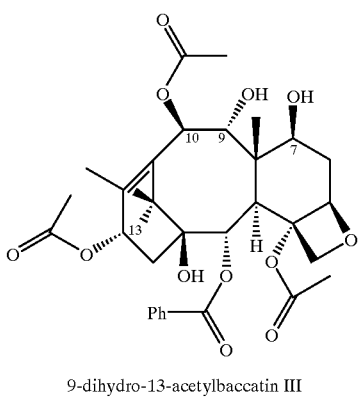

9-dihydro-13-acetylbaccatin III

The method disclosed is equally effective when using the roots or bark of the Taxus bushes but the preferred source is the needles which are in abundant supply and one of the most renewable parts of the plant.

A number of different methods have described the isolation and purification of 9-dihydro-13-acetylbaccatin III (Gunawardana G. P. el al., J. Nat. Prod 55, 1686, 1992 and Zamir et al Can. J. Chem. 73, 655, 1995). One particular advantage of using 9-dihydro-13-acetylbaccatin III as starting material is that it can be isolated by simple recrystallisations instead of the numerous silica gel column and HPLC techniques commonly used. Hence 9-dihydro-13-acetylbaccatin III can be obtained in relatively high yield, rendering it an ideal starting material for many semi-synthetic pathways.

The conversion of 9-dihydro-13-acetylbaccatin III into baccatin III involves the oxidation of the hydroxyl group at C-9 into a carbonyl group and deacetylation at C-13. The key step: the oxidation at C-9 was the main hurdle.

One major difficulty that had to be overcome was how to achieve these synthetic conversions while maintaining the integrity of the other hydroxyl groups in baccatin III, particularly the hydroxyl group at C-7. For example, direct oxidation of the hydroxyl group at C-9 on 9dihydro-13-acetylbaccatin III into a carbonyl group using the Jones' reagent (chromium trioxide and sulphuric acid) resulted in the oxidation of both C-7 and C-9 positions. In another instance, the use of pyridinium dichromate, a milder oxidizing agent than the Jones' reagent, also resulted in oxidation of the C-7 hydroxyl group with opening of the oxetane ring.

A number of different protecting groups were investigated, to prevent unwanted oxidative reactions, some of the more successful attempts included the use of certain silyl chlorides. The present invention has largely overcome this problem with the method described by the steps illustrated in Scheme 1 which can be summarised as follows:

Step A:

Compound 1, 9-dihydro-13-acetylbaccatin III, is reacted with a suitable protecting group. It is necessary to protect the hydroxyl group at position 7 of 9-dihydro-13-acetylbaccatin III, to prevent oxidation. This can be achieved through the use of silyl chlorides (eg. triethyl tri-isopropyl, t-butyldimethyl or t-butyldiphenyl) or alkyl chlorides (eg. benzyl chloride, methoxy-methyl chloride, allyl chloride or methoxy-ethyl chloride) or by the use of dihydrofuran. When t-butyldiphenyl silyl chloride is used, the above reaction yields Compound 2, 9-dihydro-13-acetyl-7-t-butyldiphenylsilyl-baccatin III, a 7-protected intermediate.

Step B:

Compound 2, the 7-protected intermediate, is then oxidized by the use of reagents such as Jones' reagent (chromium trioxide and sulphuric acid), pyridinium dichromate (PDC), pyridinium chlorochromate (PCC), Swern oxidation ($C_2O_2Cl_2$/DMSO), potassium permanganate ($KMnO_4$) or Sarret's agent ($CrO_3$/pyridine). The above oxidation procedure generates Compound 3, which contains a carbonyl moiety at C-9.

Step C:

The acetyl group at C-13 is then removed in the presence of THF and an alkyl lithium such as methyl lithium or butyl lithium to yield Compound 4, which is a 7-protected baccatin III Step D:

Compound 4, the 7-protected baccatin III can then be used as starting material for the semi-synthesis of known and novel taxanes by derivatization at C-13. This can be achieved by the use of a range of side chains (Ojima, I. et al., Tetrahedron, 48, 6985–7012, 1992; and Ojima, I. et al., Tetrahedron Letters, 34, 4149–4152, 1992).

Scheme 1

[Compound 1] → Step A → [Compound 2]

Compound 1    Compound 2

Step B ↓

[Compound 3] → Step C → [Compound 4]

Compound 3    Compound 4

Step D ↓

[Compound 5]

Compound 5

R = Ph:paclitaxel
R = OC(CH$_3$)$_3$:docetaxel
R = C(CH$_3$)CH(CH$_3$):cephlomannine
R = CH$_2$CH$_2$CH$_3$:taxcultine The success of the current invention is largely dependent upon an abundant supply of 9-dihydro-13-acetylbaccatin III which is one of the major metabolites produced by *T. canadensis*. Typically, 1.0 kg of dry needles will afford 1.0 to 2.5 g of pure 9-dihydro-13-acetylbaccatin III, making it one of the highest yielding taxanes from any taxus species known to date. The following examples therefore describe the chemical transformation of this baccatin III precursor into baccatin III derivatives which in turn can be transformed into paclitaxel and other biologically active taxanes. For a review of hydroxy protective groups the reader is directed to: T. W. Green and P. G. M. Wuts. Protective Groups In Organic Synthesis 2nd Ed.; J. Wiley and Sons, 1991, the disclosure of which is incorporated herein by reference.

Further, to assist in understanding the current invention, the following non-limiting examples are provided. The following examples should not be construed as specifically limiting the present invention, variations presently known or later developed, which would be in the understanding of one skilled in the art and considered to fall within the scope of the present invention as described herein.

EXAMPLE 1

Preparation of Compounds of Formula II (a) Preparation of 9-Dihydro-13-Acetyl-7-t-Butyl-Diphenylsilyl-Baccatin III In one procedure for making Compounds of Formula II, 9-dihydro-13-acetylbaccatin III, (63 mg; 0.1 mmol, 1 eq) was dissolved in 1 mL of dimethylformamide, to which imidazole (107 mg; 1.57 mmol; 15.7 eq) was added and the solution was stirred. t-Butyldiphenylsilylchloride (350 uL; 1.35 mmol) was added to this reaction mixture dropwise, with stirring. After being stirred for 18 hours, and the work up consisted of adding ethyl acetate, washing the organic layer with water and brine, dring over anhydrous sodium sulphate, and evaporation. The residue was subjected to silica gel chromatography with hexane and dichloromethane to obtain a 60% yield of Compound 2; 9-dihydro-13-acetyl-7-t-butyldiphenylsilyl-baccatin III.

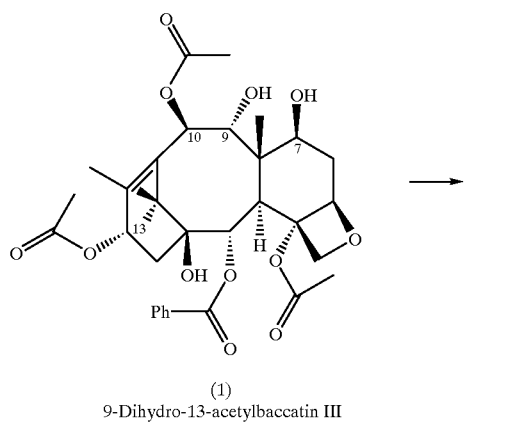

(1)
9-Dihydro-13-acetylbaccatin III

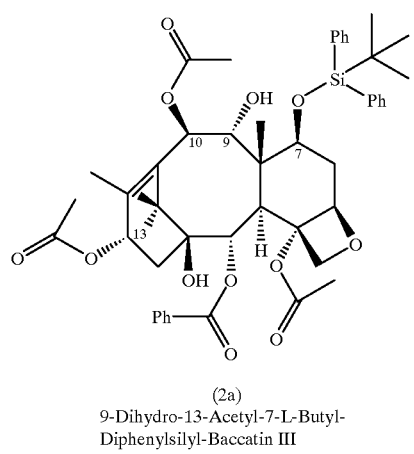

(2a)
9-Dihydro-13-Acetyl-7-L-Butyl-Diphenylsilyl-Baccatin III (b) Preparation of 9-Dihydro-13-Acetyl-7-t-Butyl-Dimethylsilyl-Baccatin III A solution of 9-dihydro-13-acetylbaccatin III (20 mg; 0.032 mmol), t-butyldimethyl-silylchloride (70 mg; 0.46 mmol) and imidazole (60 mg; 1.13 mmol) was stirred in anhydrous dimethylformamide (1.0 mL) at room temperature for 18 hours. Ethyl acetate (10 mL) was added, the solution was washed with water (3×2 mL) and dried over anhydrous magnesium sulphate. The residue was placed on a silica gel column and eluted with a gradient of ethyl acetate (33 to 50%) in hexane, affording 9dihydro-13-acetyl-7-t-butyldimethylsilyl-baccatin III (Compound 2b) as a white solid (20 mg; 0.027 mmol; 85% yield; Rf=0.66 eluting with ethyl acetate). The structure was determined by a $^1$H-NMR at 500 MHz in CDCl$_3$.

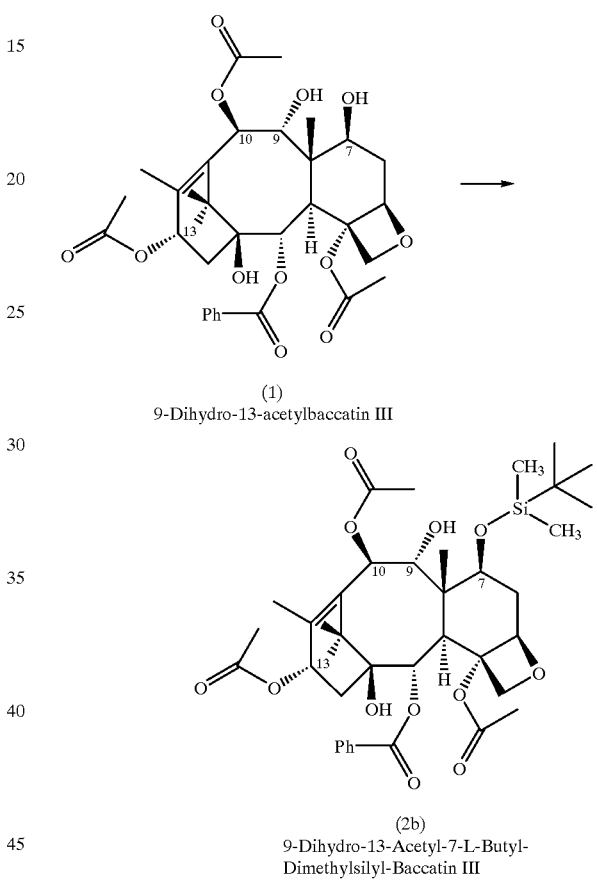

(1)
9-Dihydro-13-acetylbaccatin III (2b)
9-Dihydro-13-Acetyl-7-L-Butyl-Dimethylsilyl-Baccatin III (c) Preparation of 9-dihydro-13acetyl-7-triethylsilyl-baccatin III 9-dihydro-13-acetyl-7-triethylsilyl-baccatin III was prepared in the same manner as the other silyl derivatives just using triethylsilylchloride as reagent.

A solution of 9-dihydro-13-acetylbaccatin III (20 mg; 0.032 mmol) triethylsilychloride (50 μL; 44.9 mg; 0.30 mmol) and imidazole (60 mg; 1.13 mmol) was stirred in anhydrous dimethylformamide (1.0 mL) at room temperature for 18 hours. Ethyl acetate (10 mL) was added, the solution was washed with water (3×2 mL) and dried over anhdyrous magnesium sulphate. The residue was placed on a silica gel column and eluted with a gadient of ethyl acetate (33 to 50%) in hexane, affording 9-dihydro-13-acetyl-7-triethylsily-baccatin III (Compound 2c) as a white solid (17 mg, 0.023 mmol; 72% yield). The stucture was determined by $^1$H-NMR at 500 MHz in CDCl$_3$.

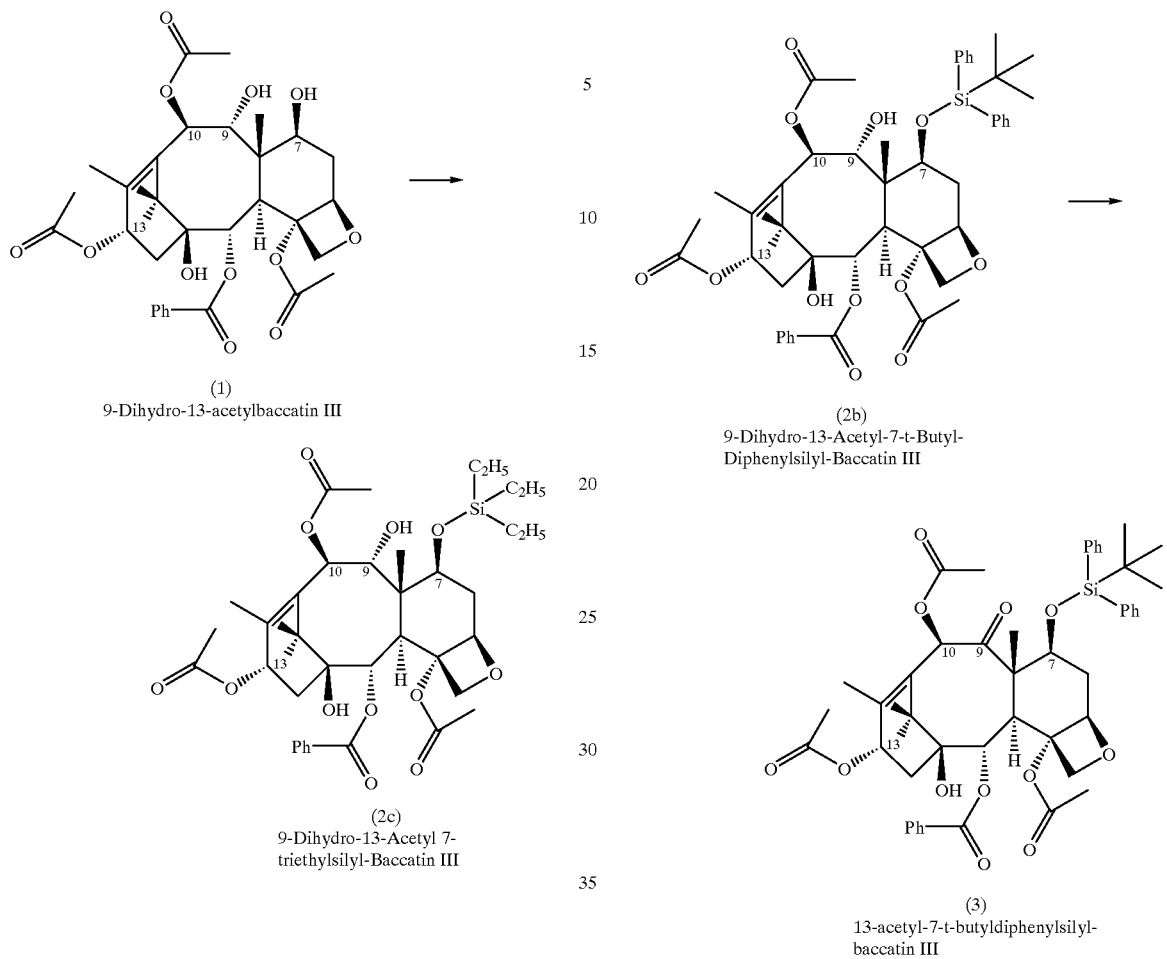

(1) 9-Dihydro-13-acetylbaccatin III (2b) 9-Dihydro-13-Acetyl-7-t-Butyl-Diphenylsilyl-Baccatin III (2c) 9-Dihydro-13-Acetyl 7-triethylsilyl-Baccatin III (3) 13-acetyl-7-t-butyldiphenylsilyl-baccatin III

EXAMPLE 2

Preparation of Compounds of Formula 3

(a) Preparation of 13-acetyl-7-t-butyldiphenylsilyl-baccatin III

One compound of Formula II, 9-dihydro-13-acetyl-7-t-butyldiphenylsilyl-baccatin III (6.0 mg) was dissolved in acetone (1.0 mL) and stirred at room temperature. To this was added 50 μL of Jones' reagent, prepared by adding 200 mg of chromium trioxide in a mixture of conc. $H_2SO_4$ and water (1 mL; 3:7 v/v), and stirred at room temperature for 30 mins. The resulting solution was worked-up by treating the reaction mixture with potassium bicarbonate and anhydrous magnesum sulphate. The crude material was then chromatographed on silica gel to obtain 5.0 mg of 13-acetyl-7-t-butyldiphenyl-silyl-baccatin III, depicted as Compound 3.

(b) Preparation of 13-acetyl-7-t-butyldiphenylsilyl-baccatin III

9-Dihydro-13-acetyl-7-t-butyldiphenylsilyl-barccatin III (0.095 g; 0.109 mmol) was dissolved in acetone (16 ml) and was stirred at 25° C. To this was added 0.79 ml of Jones' reagent, prepared by adding 200 mg of chromium trioxide in a mixture of concentrated sulfuric acid and water (1 ml; 3:7 v/v), and stirred at 25° C. for 30 min. The reaction mixture was diluted in ethyl acetate and washed with a saturated solution of $NaHCO_3$ and with brine to neutrality. The organic phase was dried ($MgSO_4$), filtered and evaporated in vacuo. The residue was flash chromatographed on silica gel with hexane:ethyl acetate (60:40) to obtain 0.073 g (77% yield) of the desired ketone.

EXAMPLE 3

Preparation of Compounds of Formula 4

(a) Preparation of 7-tert-butytdiphenylsilylbaccatin III

One of the Compounds of Formula III, 13-acetyl-7-t-butyldiphenyl-silyl-baccatin III (5.0 mg) was dissolved in a polar donor solvent such as tetrahydrofuran (500 μL). After cooling the reaction mixture to −78° C. 50 μL of 1.4 M methyl lithium in ether was added and the solution stirred for 1.5 hours. The reaction mixture was then quenched with aqueous sodium acetate and worked-up with ethyl acetate. The crude reaction mixture was subjected to HPLC and three compounds were isolated. The desired product, 7-tert-butyidiphenylsilylbaccatin III, depicted as Compound 4, was purified using preparative HPLC (RP-18 column) gradient (100 min; 25% MeCN to 100% MeCN) with a retention time of 81 min.

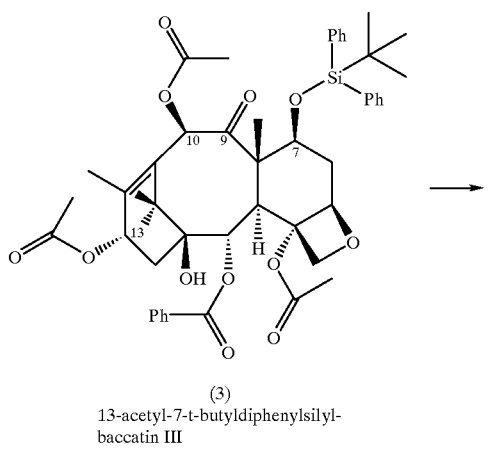

(3)
13-acetyl-7-t-butyldiphenylsilyl-baccatin III

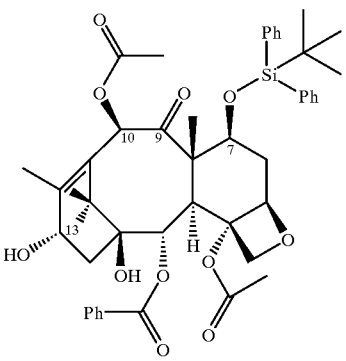

(4)
7-t-butyldiphenylsilyl-baccatin III (b) Preparation of 7-t-butyldiphenylsilyl-baccatin III 13-Acetyl-7-t-butyldiphenylsilyl-baccatin III (0.080 g; 0.092 mmol) was dissolved in tetrahydrofuran (18 ml) and cooled to −44° C. To this was added a 2.5 M solution of n-BuLi in hexanes (0.115 ml; 0.288 mmol), and stirred for 1.5 h at −44° C. n-BuLi (0.120 ml) was added again and the reaction was stirred for an additional 1.5 h. The reaction was then quenched with brine and extracted with ethyl acetate which was dried (MgSO$_4$), filtered and evaporated in vacuo. The residue was flash chromatographed on silica gel with hexane:ethyl acetate (gradient of 60:40 to 50:50) to obtain 0.022 g (46% yield based on recovered starting material).

EXAMPLE 4

Conversion of a Compound of Formula 4 into a Taxane

Conversion of the 7-protected baccatin III into paclitaxel, docetaxol or canadenisol is conducted according to the references of Ojima et al., (previously cited) and following the steps described below.

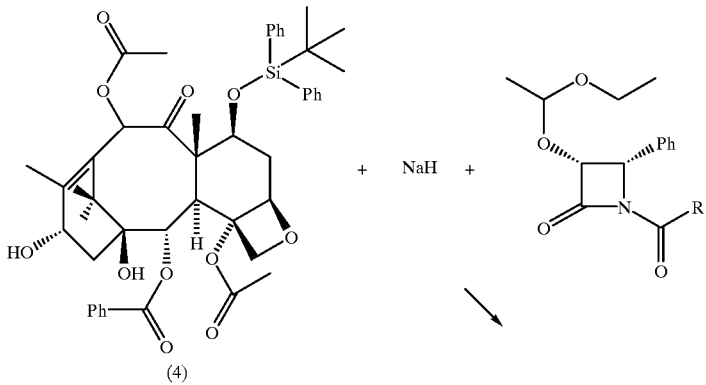

(4)
7-t-butyldiphenylsilylbaccatin III

-continued

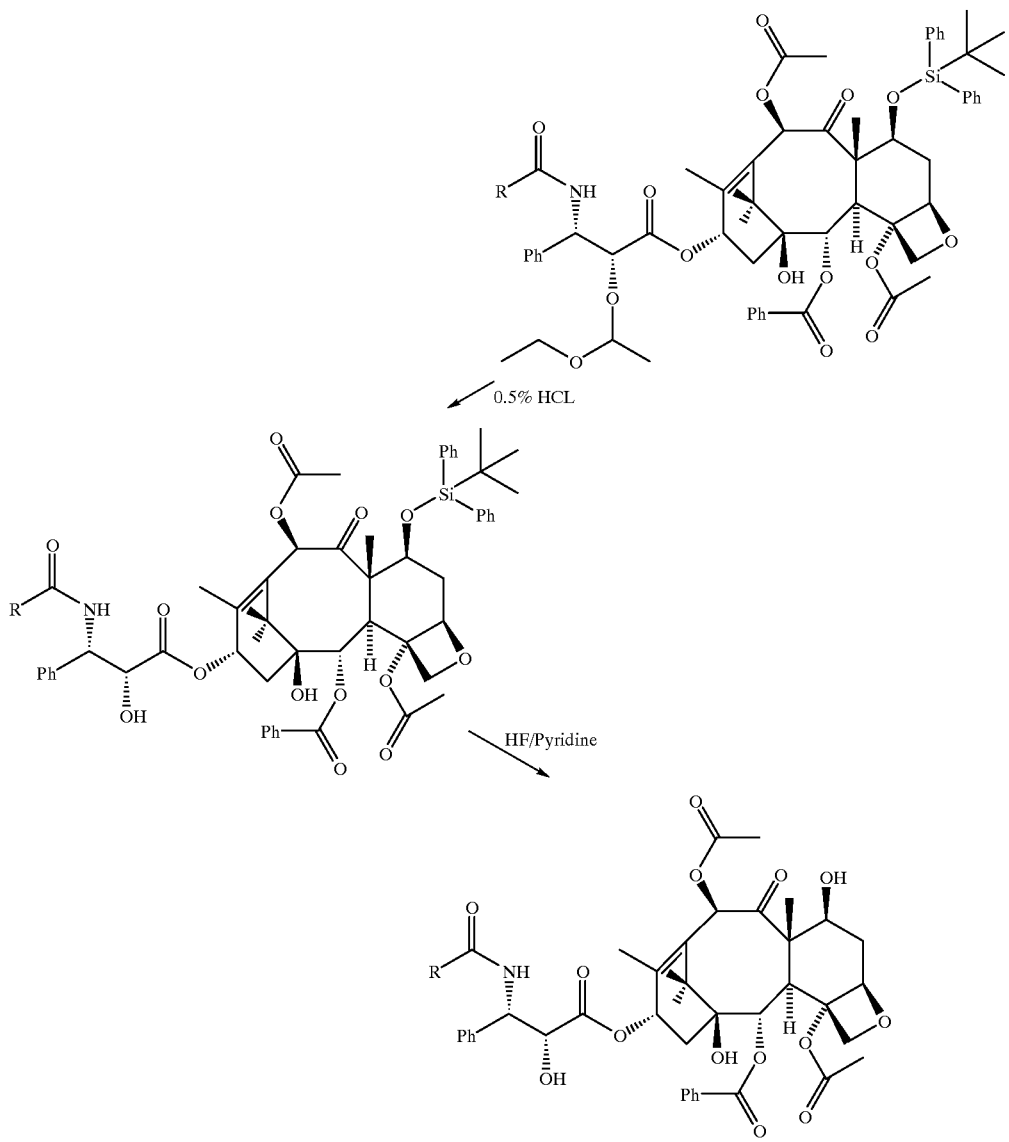

R = Ph:paclitaxel
R = OC(CH$_3$)$_3$:docetaxel
R = C(CH$_3$)CH(CH$_3$):cephlomannine
R = CH$_2$CH$_2$CH$_3$:taxcultine

EXAMPLE 5

Deprotection of a 7-hydroxy Group

Preparation of Baccatin III 7-t-Butyldiphenylsilyl-baccatin III (0.010 g; 0.012 mmol) was dissolved in 1.5 ml 95% ethanol and was treated with concentrated HCI (0.040 ml; 0.3 M HCI in ethanol). After stirring at 25° C. for 24 h, the mixture was neutralized with saturated NaHCO$_3$ and extracted with ethyl acetate which was dried (MgSO$_4$), filtered and evaporated in vacuo.

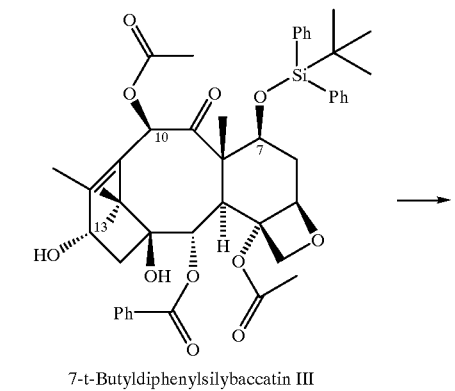

7-t-Butyldiphenylsilybaccatin III

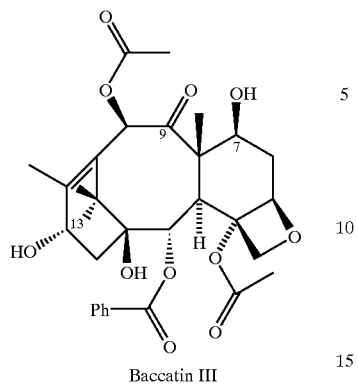

Baccatin III

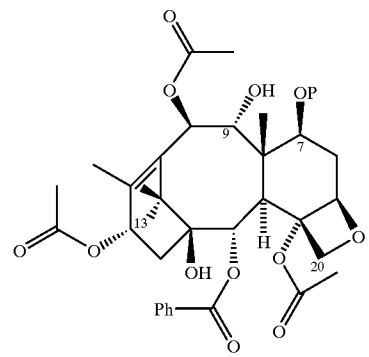
I

It is to be understood that the examples described above are not meant to limit the scope of the present invention. It is expected that numerous variants will be obvious to the person skilled in the art to which the present invention pertains, without any departure from the spirit of the present invention. The appended claims, properly construed, form the only limitation upon the scope of the present invention.

The embodiments in which an exclusive property and privilege is claimed are defined as follows:

1. A process for the preparation of a taxane of formula (III)

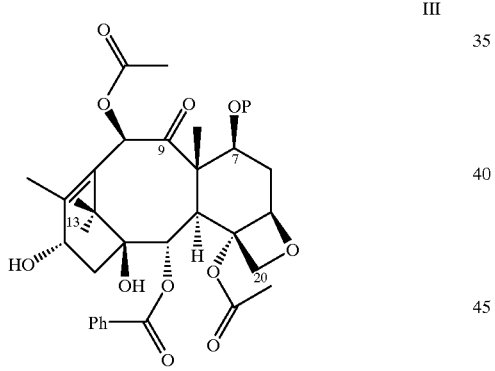
III which comprises the steps of:

(i) protecting the hydroxy group at the 7-position of 9-dihydro-13-acetylbaccatin III;

(ii) oxidizing the hydroxy group at the 9-position of 9-dihydro-13-acetylbaccatin III;

(iii) deacylating the ester at the 13-position to form a 13-hydroxy compound of formula III, wherein P is a protecting group.

2. A process according to claim 1, which additionally comprises a step of removing the hydroxy protecting group P at the 7-position to yield baccatin III.

3. A process for the preparation of a 7-protected-9-dihydro-13-acetylbaccatin of formula I wherein P is a hydroxy protecting group, which comprises the step of reacting 9-dihydro-13-acetylbaccatin III with a protecting group to form a compound of formula I.

4. The process of claim 3, wherein said protecting group is a silyl chloride, an alkyl chloride or dihydrofuran.

5. A process for the preparation of a compound of formula II

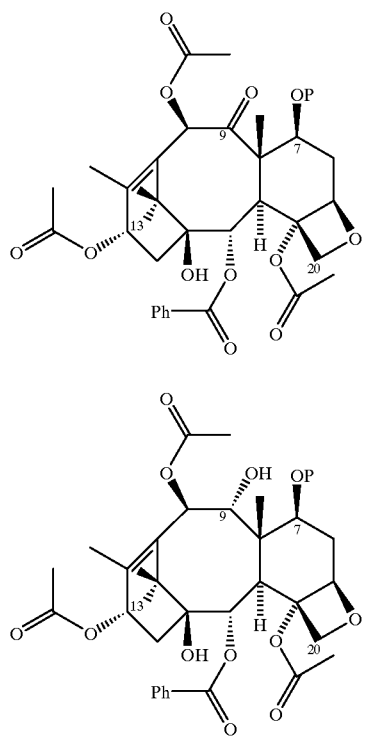

which comprises the step of oxidizing a compound of formula I.

6. A process for the preparation of a compound of formula III from a compound of formula II

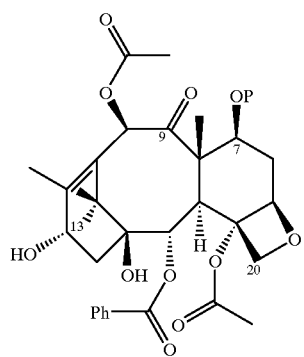

wherein P is a hydroxy protecting group, which comprises converting a 13-acetyl group to 13-hydroxyl group by treating the compound of formula II with an alkyl lithium followed by aqueous workup.

7. The process according to claim 4, wherein the silyl chloride is t-butyldiphenylsilyl-chloride, t-butyldimethylsilylchloride, or triisopropylsilylchloride.

8. The process according to claim 5, wherein said oxidizing is accomplished with Jones' reagent, pyridinium, dichromate, Swern oxidation, potassium permanganate or Sarret's reagent.

9. The process according to claim 6, wherein said alkyl lithium is n-butyllithium.

10. The process according to claim 6, wherein said alkyl lithium is methyl lithium.

* * * * *